(12) United States Patent
Margot et al.

(10) Patent No.: US 7,022,735 B2
(45) Date of Patent: Apr. 4, 2006

(54) PLANT PROTECTION AGENTS

(75) Inventors: Paul Margot, Biel-Benken (CH); Gertrude Knauf-Beiter, Müllheim (DE)

(73) Assignee: Bayer Aktiengesellschaft, Leverkusen (DE)

( * ) Notice: Subject to any disclaimer, the term of this patent is extended or adjusted under 35 U.S.C. 154(b) by 294 days.

(21) Appl. No.: 10/191,584

(22) Filed: Jul. 9, 2002

(65) Prior Publication Data

US 2003/0083340 A1 May 1, 2003

Related U.S. Application Data

(62) Division of application No. 09/888,806, filed on Jun. 25, 2001, now Pat. No. 6,441,031, which is a division of application No. 09/319,550, filed on Jun. 8, 1999, now Pat. No. 6,294,543.

(30) Foreign Application Priority Data

Dec. 13, 1996 (CH) .................................. 3072/96
May 26, 1997 (CH) .................................. 1229/97

(51) Int. Cl.
A01N 37/12 (2006.01)
A01N 37/24 (2006.01)
A01N 37/44 (2006.01)

(52) U.S. Cl. ........................ 514/539; 514/613
(58) Field of Classification Search ................ 514/537, 514/539, 613
See application file for complete search history.

(56) References Cited

U.S. PATENT DOCUMENTS

| 5,059,623 A | 10/1991 | Krüger et al. | 514/613 |
| 5,563,168 A * | 10/1996 | Brand et al. | 514/357 |
| 5,569,656 A | 10/1996 | Dutzmann et al. | |

FOREIGN PATENT DOCUMENTS

| AU | 633735 | 12/1991 |
| AU | 3317395 | 5/1996 |
| AU | 42601/96 | 7/1996 |
| CA | 2119992 | 9/1994 |
| DE | 4437048 | 4/1996 |
| DE | 4444911 | 6/1996 |
| DE | 19543746 | 5/1997 |
| EP | 460575 | 12/1991 |
| EP | 616771 | 9/1994 |
| EP | 627163 | 12/1994 |
| EP | 741970 | 11/1996 |
| GB | 2279568 | 1/1995 |
| WO | WO 96/03047 | 2/1996 |
| WO | WO 97/00011 | 1/1997 |
| WO | WO 97/01277 | 1/1997 |
| WO | WO 97/06677 | 2/1997 |
| WO | WO 97/40674 | 11/1997 |

OTHER PUBLICATIONS de Fraine, Paul J. et al., vol. 44, No. 1, May 1995, pp. 77-79, XP002020496.
Derwent Abstract 95-81855, XP 002020497.
Research Disclosure, No. 390, pp. 673-674, Oct. 1996, XP000639940.
Research Disclosure, No. 348, p. 267, Apr. 1, 1993, XP000304224.
Verified English Translation of AU 67024/96.
Verified English Translation of AU 76268/96.
Verified English Translation of AU 29834/95.

* cited by examiner

*Primary Examiner*—S. Mark Clardy
(74) *Attorney, Agent, or Firm*—Richard E. L. Henderson; John E. Mrozinski, Jr.

(57) ABSTRACT

The present invention provides a microbicide composition for plants, containing at least two active ingredient components in an amount producing synergistic activity, together with an appropriate filler, wherein component I is the compound 2-[.alpha.-{[(.alpha.-methyl-3-trifluoromethyl-benzyl)imino]-oxy}-o-tolyl]-yoxylic acid-methylester-O-methyloxime, and component II is a compound selected from the group consisting of benzo(1,2,3)thiadiazole-7-car-bothio-acid-S-methylester ("Acibenzolar-S-methyl"); 3-anilino-5-methyl-5-(4-phenoxyphenyl)-1,3-oxazolidine-2,4-dione ("Famoxadone"); 4-(2,2-difluoro-1,3-benzo-dioxol-4-yl)pyrrole-3-carbonitrile ("Fludioxonil"); 4-(2,3-dichlorophenyl)pyrrole-3-carbonitrile ("Fenpiclonil"); 1-methyl-cyclohexanecarboxylic acid-(2,3-dichloro-4-hydroxy-phenyl)-amide ("Fenhexamid"); 2-{2-[6-(2-cyano-phenoxy)-pyrimidin-4-yloxy]-phenyl}-3-methoxy-acrylic acid methyl ester ("Azoxystrobin"); Methoximino-(2-o-tolyloxymethyl-phenyl)-acetic acid methyl ester ("Kresoxim-methyl"); or respectively one of the salts or metal complexes of components I and II. The composition of the present invention finds use as a plant protection agent.

3 Claims, No Drawings

PLANT PROTECTION AGENTS

This application is a divisional of U.S. Ser. No. 09/888,806 filed on Jun. 25, 2001 now U.S. Pat. No. 6,441,031, which is itself a divisional of U.S. Ser. No. 09/319,550 filed on Jun. 8, 1999, now U.S. Pat. No. 6,294,543.

FIELD OF THE INVENTION

The present invention relates to new plant-protecting active ingredient mixtures having synergistically increased activity, containing at least two active ingredient components, and a process for the application of such mixtures in plant protection, especially in the control and prevention of disease outbreaks.

DETAILED DESCRIPTION OF THE INVENTION

Component I is the compound
2-[α-{[(α-methyl-3-trifluoromethyl-benzyl)imino]-oxy}-o-tolyl]-glyoxylic acid-methylester-O-methyloxime, (EP-A-460,575); and
component II is a compound selected from the group
IIA) 5,7-dichloro-4-(4-fluorophenoxy)quinoline ("Quinoxyfen") (EP-A-326,330);
IIB) 4-cyclopropyl-6-methyl-N-phenyl-2-pyrimidinamine ("Cyprodinil") (The Pesticide Manual, 10th. edition, 1994, 109);
IIC) benzo(1,2,3)thiadiazole-7-carbothio-acid-S-methylester "Acibenzolar-S-methyl") (EP-A-313,512);
IID) 3-anilino-5-methyl-5-(4-phenoxyphenyl)-1,3-oxazolidine-2,4-dione ("Famoxadone") (EP-A-393,911);
IIE) 8-(1,1-dimethylethyl)-N-ethyl-N-propyl-1,4-dioxaspiro[4.5]decane-2-methanamine ("Spiroxamin") (EP-A-281,842);
IIF) 4-(2,2-difluoro-1,3-benzodioxol-4-yl)pyrrole-3-carbonitrile ("Fludioxonil") (The Pesticide Manual, 10th. edition, 1994, 326);
IIG) 4-(2,3-dichlorophenyl)pyrrole-3-carbonitrile ("Fenpiclonil") (The Pesticide Manual, 10th. edition, 1994, 302);
IIH) 1-methyl-cyclohexanecarboxylic acid-(2,3-dichloro-4-hydroxy-phenyl)-amide ("Fenhexamid") (EP-A-339,418);
IIJ) 2-{2-[6-(2-cyano-phenoxy)-pyrimidin-4-yloxy]-phenyl}-3-methoxy-acrylic acid methyl ester ("Azoxystrobin") (EP-A-382,375);
IIK) Methoximino-(2-o-tolyloxymethyl-phenyl)-acetic acid methyl ester ("Kresoxim-methyl") (EP-A-398,692); or respectively one of the salts or metal complexes of components I and II.

It has now surprisingly been shown that the mixtures of components I and II according to the invention display not only additive action, but significant synergistically increased action in the prevention and control of plant diseases.

Favourable mixture ratios of the two active ingredients are I:II=20:1 to 1:20, preferably I:II=10:1 to 1:10, 6:1 to 1:6, 2:1 to 1:10 and 10:1 to 1:2.

The active ingredient mixtures I+II according to the invention have very advantageous properties in the protection of plants against the outbreak of disease.

In addition, mixtures with compound IIc can activate the defence system, which is latent in the plant, against pathogenic microbial influences and can thus protect the plant by immunisation.

With the present active ingredient mixtures, the microorganisms appearing on plants or plant parts (fruits, flowers, foliage, stems, tubers, roots) of different useful plants can be stopped or destroyed, whereby plant parts growing later also remain free from such microorganisms. They may also be used as dressings for the treatment of plant propagation material, especially seeds (fruits, tubers, seed grain) and plant cuttings (e.g. rice) to provide protection from fungal infections, and against phytopathogenic fungi appearing in the soil. The active ingredient mixtures according to the invention are notable for their especially good plant tolerance and their environmental acceptability.

The active ingredient mixtures according to the invention are effective against the following classes of related phytopathogenic fungi: ascomycetes (e.g. *Venturia, Podosphaera, Erysiphe, Monilinia, Mycosphaerella, Uncinula*); basidiomycetes (e.g. the genus *Hemileia, Rhizoctonia, Puccinia*); *Fungi imperfecti* (e.g. *Botrytis, Helminthosporium, Rhynchosporium, Fusarium, Septoria, Cercospora, Alternaria, Pyricularia* and in particular *Pseudocercosporella herpotrichoides*); oomycetes (e.g. *Phytophthora, Peronospora, Bremia, Pythium, Plasmopara*).

Target crops for the indicated fields disclosed herein are, within the context of this invention, e.g. the following species of plants: cereals (wheat, barley, rye, oats, rice, sorghum and the like); beets: (sugar beet and fodder beet); pip, stone and berry fruit: (apples, pears, plums, peaches, almonds, cherries, strawberries, raspberries and blackberries); leguminous plants: (beans, lentils, peas, soybeans); oil plants: (rape, mustard, poppy, olives, sunflowers, coconut, castor oil plant, cacao, peanut); cucumber plants (gourds, cucumbers, melons); fibre plants: (cotton, flax, hemp, jute); citrus fruits: (oranges, lemons, grapefruit, mandarins); vegetable varieties (spinach, lettuce, asparagus, cabbage varieties, carrots, onions, tomatoes, potatoes, peppers); Lauraceae: (avocado, cinnamon, camphor) or plants such as maize, tobacco, nuts, coffee, sugar cane, tea, grapevines, hops, banana and natural rubber plants, as well as ornamental plants (flowers, shrubs, deciduous trees and coniferous trees such as conifers).

This is not intended to be a limiting list of plants. The active ingredient mixtures according to the invention are especially advantageous for the following applications:
I+IIA: for cereals and vines;
I+IIB: for cereals, particularly wheat and barley, also for vines, vegetables and fruit;
I+IIC: for cereals;
I+IID: for vines;
I+IIE: for cereals;
I+IIF: for cereals, particularly wheat and barley, also for vines and vegetables;
I+IIG: for treatment of seeds;
I+IIH: for vegetables and vines;
I+IIJ: for cereals and vines;
I+IIK: for cereals, particularly for wheat and barley.

The active ingredient mixtures of formulae I and II are normally employed in the form of compositions. The active ingredients of formulae I and II may be applied to the area or plants to be treated either simultaneously or in succession on the same day, together with further optional fillers, surfactants or other application-enhancing additives which are customary in formulation techniques.

Appropriate fillers and additives may be solid or liquid, and correspond to the substances which are efficient in formulation techniques, e.g. natural or regenerated mineral substances, solvents, dispersants, wetting agents, adhesion agents, thickeners, binding agents or fertilisers.

A preferred method of applying an active ingredient mixture containing at least one of each of these active ingredients I and II is application to the parts of the plant above ground, especially the leaf system (leaf application). The number of applications and application rate depend on the biological and climatic living conditions of the instigator. However, the active ingredients may also reach the plant through the root system (systemic action) via the soil or the water, whereby the plant site is drenched with a liquid formulation (e.g. in rice cultivation) or the substances are incorporated into the soil in solid form, e.g. in the form of granules (soil application). The compounds of formulae I and II may also be applied to seed grain in a seed treatment (coating), whereby the tubers or grains are either immersed in succession with a liquid formulation of each active ingredient, or are coated with an already combined, wet or dry formulation. In addition, in particular cases, further types of plant application are possible, e.g. the targeted treatment of buds or syncarpy. Here, the compounds of the combination are used in unchanged form or preferably together with excipients which are usual in formulation techniques, and they are processed in known manner e.g. into emulsion concentrates, coatable pastes, directly sprayable or diluable solutions, diluted emulsions, wettable powders, soluble powders, dusts, granules, or by encapsulation into, for example, polymeric substances. The application methods, such as spraying, misting, dusting, dispersing, coating or drenching, are selected according to the targeted aims and the given conditions, in the same way as for selection of the type of agent. Favourable application rates for the active ingredient mixture are in general 50 g to 2 kg active substance per ha, especially 100 g to 700 g active substance per ha, most preferably 75 g to 450 g active substance per ha. For the treatment of seeds, the application rates are 0.5 g–600 g, preferably 5 g–80 g active substance per 100 kg seeds.

The formulations are produced in known manner, e.g. by intimately mixing and/or grinding the active ingredients with diluting agents, e.g. solvents, solid fillers, and optionally surface-active compounds (surfactants).

The solvents in question may be: aromatic hydrocarbons, preferably fractions $C_8$ to $C_{12}$, such as xylene mixtures or substituted naphthalenes, phthalic acid esters such as dibutyl or dioctyl phthalate, aliphatic hydrocarbons such as cyclohexane or paraffins, alcohols and glycols, as well as the ethers and esters thereof, such as ethanol, ethylene glycol, ethylene glycol monomethyl ether or monoethyl ether, ketones such as cyclohexanone, strongly polar solvents such as N-methyl-2-pyrrolidone, dimethyl sulphoxide or dimethyl formamide, as well as optionally epoxidated vegetable oils such as epoxidated coconut oil or soybean oil; or water.

The solid fillers, e.g. for dusting agents and dispersible powders, are normally natural mineral powder, such as calcitol, talcum, kaolin, montmorillonite or attapulgite. To improve the physical properties, highly disperse silicic acid or highly disperse, absorbent polymerisates may also be added. The granulated, adsorptive granulate fillers may be porous types such as pumice stone, brick fragments, sepiolite or bentonite, and non-sorptive fillers are e.g. calcitol or sand.

Furthermore, a number of pregranulated materials of inorganic or organic nature may also be used, especially dolomite or pulverised plant residues.

Depending on the type of active ingredients of formulae I and II be formulated, the surface-active compounds may be non-ionic, cationic and/or anionic surfactants with good emulsifying, dispersing and wetting properties. By surfactants are also understood surfactant mixtures.

Especially advantageous, application-enhancing admixtures are also natural or synthetic phospholipids from the series cephalins and lecithins, e.g. phosphatidylethanolamine, phosphatidylserine, phosphatidylglycerol, lysollecithin.

The agrochemical compositions normally contain 0.1 to 99%, especially 0.1 to 95% active ingredients of formulae I and II, 99.9 to 1%, especially 99.9 to 5% of a solid or liquid additive and 0 to 25%, especially 0.1 to 25% of a surfactant.

While concentrated formulations are preferred as commercial products, the final user normally uses diluted formulations.

The following examples serve to illustrate the invention, whereby "active ingredient" indicates a mixture of compound I and compound II in a certain mixture ratio.

FORMULATION EXAMPLES

| Wettable powder | a) | b) | c) |
|---|---|---|---|
| active ingredient [I:II = 1:3(a), 1:2(b), 1:1(c)] | 25% | 50% | 75% |
| Na ligninsulphonate | 5% | 5% | — |
| Na laurylsulphate | 3% | — | 5% |
| Na diisobutylnaphthalenesulphonate | — | 6% | 10% |
| octylphenol-polyethylene-glycol-ether (7–8 mols ethylene oxide) | — | 2% | — |
| highly disperse silicic acid | 5% | 10% | 10% |
| kaolin | 62% | 27% | — |

The active ingredient is mixed well with the additives and ground thoroughly in an appropriate mill. Spray powders are obtained, which can be diluted with water to form suspensions of any desired concentration.

| Emulsifiable concentrate | |
|---|---|
| active ingredient (I:II = 1:6) | 10% |
| octylphenol polyethylene glycol ether (4–5 mols ethylene oxide) | 3% |
| Ca dodecyl-benzene-sulphonate | 3% |
| castor oil polyglycol ether (35 mols ethylene oxide) | 4% |
| cyclohexanone | 30% |
| xylene mixture | 50% |

Emulsions of any desired dilution may be produced from this concentrate by diluting it with water, and they can be used in plant protection.

| Coated granule | |
|---|---|
| active ingredient (I:II = 1:10) | 8% |
| polyethylene glycol (molecular weight 200) | 3% |
| kaolin | 89% |

The finely ground active ingredient is applied evenly to the kaolin which is moistened with polyethylene glycol, in a mixer. In this way, dust-free coated granules are obtained.

BIOLOGICAL EXAMPLES

A synergistic effect is present if the activity of the active ingredient combination is greater than the sum of activities of the individual components.

The activity E to be expected for a given active ingredient combination obeys the so-called COLBY formula and may be calculated as follows (COLBY, S. R. "Calculating synergistic and antagonistic responses of herbicide combination". Weeds, Vol.15, pages 20–22; 1967):

ppm=milligrams active ingredient (=ai) per liter spray mixture
X=% activity from active ingredient I during application of p ppm of active ingredient
Y=% activity from active ingredient II during application of q ppm of active ingredient The expected (additive) activity of active ingredients I+II during application of p+p ppm active ingredient is, according to Colby $$E = X + Y - \frac{X \cdot Y}{100}$$

If the activity actually observed (O) is greater than the expected activity (E), then the combination is super-additive in its activity, i.e. there is a synergistic effect (SF=synergie factor).

B-1

Activity Against *Puccinia recondita* on Wheat a) Residual Protective Activity

Wheat plants are sprayed until dripping wet, 6 days after sowing, with an aqueous spray mixture prepared from wettable powder of the active ingredient mixture, and are infected 24 hours later with a uredospore suspension of the fungus. After an incubation period of 48 hours (conditions: 95 to 100% relative atmospheric humidity at 20° C.), the plants are placed in a greenhouse at 22° C. 12 days after infection, the fungal attack is evaluated.

b) Systemic Activity 5 days after sowing, an aqueous spray mixture prepared from wettable powder of the active ingredient mixture is poured onto wheat plants. Care is taken that the spray mixture does not come into contact with the parts of the plants that are above ground. 48 hours later, the plants are infected with a uredospore suspension of the fungus. After an incubation period of 48 hours (conditions: 95 to 100% relative atmospheric humidity at 20° C.), the plants are placed in a greenhouse at 22° C. 12 days after infection, the fungal attack is evaluated.

Active ingredient mixtures comprising components IIB and IIC in particular demonstrate good synergistic activity.

Example B-2

Activity Against *Plasmopara viticola* on Vines

Vine seedlings at the 4 to 5 leaf stage are sprayed until dripping wet with an aqueous spray mixture prepared from wettable powder of the active ingredient mixture, and are infected 24 hours later with a sporangia suspension of the fungus. The fungal attack is evaluated 6 days after infection, during which period the conditions of 95 to 100% relative atmospheric humidity and a temperature of 20° C. are maintained.

Active ingredient mixtures comprising components IIB, IID and IIA in particular demonstrate good synergistic activity.

Example B-3

Activity Against *Erysiphe graminis* on Barley a) Residual Protective Activity

Barley plants of approximately 8 cm height are sprayed until dripping wet with an aqueous spray mixture prepared from wettable powder of the active ingredient mixture, and 3 to 4 hours later are dusted with conidia of the fungus. The infected plants are placed in a greenhouse at 22° C. 12 days after infection, the fungal attack is evaluated.

b) Systemic Activity

An aqueous spray mixture prepared from wettable powder of the active ingredient mixture is poured onto barley plants of approximately 8 cm height. Care is taken that the spray mixture does not come into contact with the parts of the plants that are above ground. 48 hours later, the plants are dusted with conidia of the fungus. The infected plants are placed in a greenhouse at 22° C. 12 days after infection, the fungal attack is evaluated. Active ingredient mixtures comprising components IIA, IID and IIE in particular demonstrate good synergistic activity.

TABLE 1

Active ingredient IIA = Quinoxyfen

| Test No. | active ingredient I mg/liter | active ingredient IIA mg/liter | ratio I:II | % activity found O | % activity calculated E | SF O/E |
|---|---|---|---|---|---|---|
| 0 | — | — | | 0 (control) | | |
| 1 | 0.1 | — | | 6 | | |
| 2 | 1.0 | — | | 30 | | |
| 3 | — | 0.1 | | 4 | | |
| 4 | — | 0.5 | | 6 | | |
| 5 | — | 1.0 | | 8 | | |
| 6 | — | 10.0 | | 21 | | |
| 7 | 0.1 | 0.1 | 1:1 | 26 | 10 | 2.6 |
| 8 | 0.1 | 0.5 | 1:5 | 30 | 12 | 2.5 |
| 9 | 0.1 | 1.0 | 1:10 | 21 | 14 | 1.5 |
| 10 | 1.0 | 10.0 | 1:10 | 75 | 45 | 1.7 |

Example B-4

Activity Against *Phytophthora infestans* on Tomatoes a) Curative Activity

Tomato plants of the variety "red gnome" are sprayed with a zoospore suspension of the fungus after cultivating for three weeks, and incubated in a cabin at 18 to 20° C. and under saturated atmospheric humidity. The humidity is stopped after 24 hours. After drying off the plants, they are sprayed with a mixture which contains the active substances formulated as a wettable powder. When the spray coating has dried on, the plants are again placed in the moist cabin for 4 days. The number and size of typical leaf spots which have appeared after this period are the criterion for evaluating the efficacy of the tested substances.

b) Preventive Systemic Activity

The active substances formulated as wettable powders are applied to the surface of the soil of three week old tomato plants of the variety "red gnome" which have been potted into single pots. After leaving for three days, the undersides of the leaves of the plants are sprayed with a zoospore suspension of *Phytophthora infestans*. They are then kept for 5 days in a sprayed cabin at 18 to 20° C. and under saturated atmospheric humidity. After this period, typical leaf spots appear. The number and size thereof serve to evaluate the efficacy of the tested substances.

Active ingredient mixtures comprising components IIB and IIC in particular demonstrate good synergistic activity.

Example B-5

Activity Against *Botrytis cinerea* on Apple Fruits. Residual Protective Action

Artificially damaged apples are treated by applying a spray mixture to the wound sites in drops. The treated fruits are then inoculated with a spore suspension of the fungus and incubated for one week at high atmospheric humidity and ca. 20° C. The fungicide action of the test substance is deduced from the number of wound sites that have started to rot. Active ingredient mixtures comprising components IIB and IIC in particular demonstrate good synergistic activity.

Example B-6

Activity Against *Fusarium nivale* on Rye (Seed Treatment)

Rye of the variety "Tetrahell" which is naturally infected with Fusarium nivale is dressed with the fungicide to be tested on a mixing roller, whereby the following concentrations are used: 20 or 6 ppm AS (based on the weight of the seeds).

The infected and treated rye is sown in the open in October with a seed drilling machine on plots of 3 m length and 6 seed rows. 3 repeats per concentration. Up to evaluation of the attack, the test plantation is cultivated under normal field conditions (preferably in a region with a closed snow cover during the winter months).

To evaluate the phytotoxicity, an appraisal is made of the seed emergence in the autumn and an appraisal is made in spring of the crop density/number of plants.

To determine the active ingredient activity, the percentage of plants attacked by *Fusarium* is counted in spring, directly after the snow has thawed. The active ingredient mixtures demonstrate good synergistic activity.

The foregoing embodiments of the present invention are offered for the purpose of illustration and not limitation. It will be apparent to those skilled in the art that the embodiments described herein may be modified or revised in various ways without departing from the spirit and scope of the invention. The scope of the invention is to be measured by the appended claims.

What is claimed is:

1. A microbicide composition for plants containing in synergistically effective amounts the compounds 2-[α-{[(α-methyl-3-trifluoromethyl-benzyl)imino]-oxy}-o-tolyl]-glyoxylic acid-methylester-O-methyloxime (trifloxystrobin) and 1-methyl-cyclohexanecarboxylic acid-(2,3-dichloro-4-hydroxy-phenyl)-amide (fenhexamid) and, optionally, one or more fillers, surfactants, and/or other additives.

2. The composition according to claim 1 wherein the weight ratio of trifloxystrobin to fenhexamid is 20:1 to 1:20.

3. A method for the control of plant diseases comprising applying a synergistically effective amount of the composition according to claim 1 to a plant site or plant locus simultaneously, in succession, or on the same day.

* * * * *